United States Patent
Pastwik

(10) Patent No.: US 6,816,254 B2
(45) Date of Patent: Nov. 9, 2004

(54) FLOW CELL CLAMP

(75) Inventor: Lawrence R. Pastwik, Tonawanda, NY (US)

(73) Assignee: Richert, Inc., Depew, NY (US)

( * ) Notice: Subject to any disclaimer, the term of this patent is extended or adjusted under 35 U.S.C. 154(b) by 0 days.

(21) Appl. No.: 10/207,547

(22) Filed: Jul. 29, 2002

(65) Prior Publication Data

US 2004/0017564 A1 Jan. 29, 2004

(51) Int. Cl.[7] .............................................. G01N 1/10
(52) U.S. Cl. ...................................................... 356/246
(58) Field of Search ................................ 356/246, 244, 356/317–319, 73, 39, 446; 422/100–104, 50, 70, 99; 435/6, 7.1

(56) References Cited

U.S. PATENT DOCUMENTS

| | | | |
|---|---|---|---|
| 3,684,386 A | * | 8/1972 | Noll ............................ 356/246 |
| 3,778,165 A | | 12/1973 | Grubb et al. |
| 4,889,427 A | | 12/1989 | Van Veen et al. |
| 5,313,264 A | | 5/1994 | Ivarsson et al. |
| 5,398,110 A | | 3/1995 | Kitaoka |
| 5,485,277 A | | 1/1996 | Foster |
| 5,763,191 A | | 6/1998 | Knoll et al. |
| 6,444,175 B1 | * | 9/2002 | Singh-Gasson et al. ..... 422/102 |

FOREIGN PATENT DOCUMENTS

WO      WO00/29830      5/2000

* cited by examiner

*Primary Examiner*—Tu T. Nguyen
(74) *Attorney, Agent, or Firm*—Hodgson Russ LLP

(57) ABSTRACT

A flow cell clamp for clamping a flow cell body generally includes a flow cell retainer operatively arranged to hold a flow cell body and a U-shaped clamping member operatively arranged to apply a clamping force to the flow cell body for holding the flow cell body securely within the flow cell retainer.

4 Claims, 9 Drawing Sheets

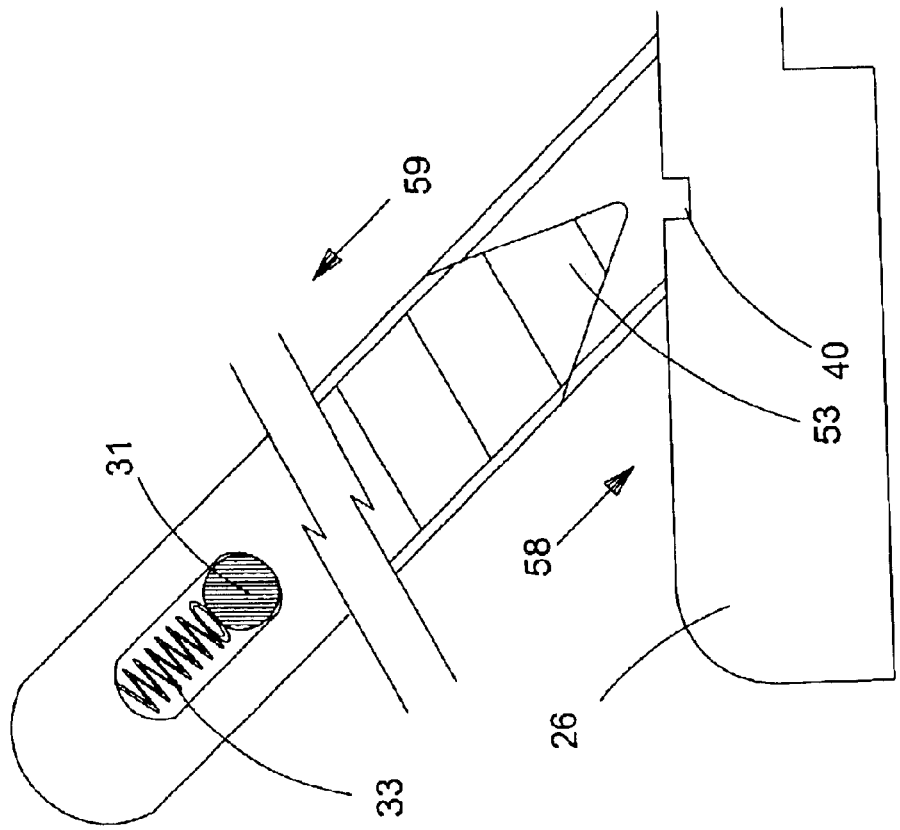
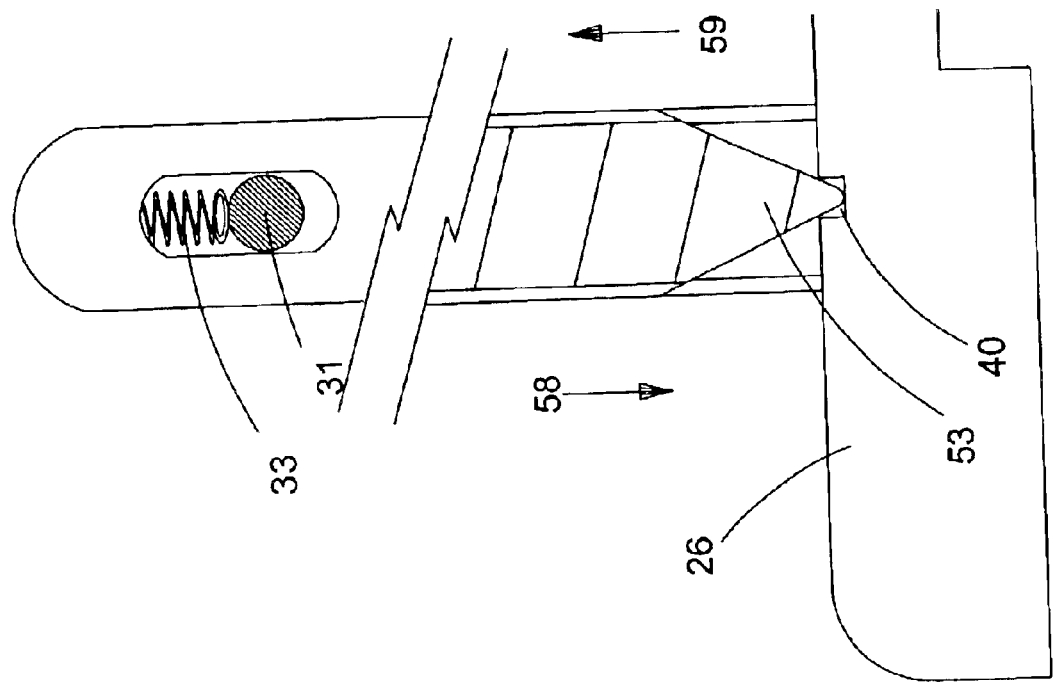
Fig. 8

FLOW CELL CLAMP

FIELD OF THE INVENTION

The present invention relates generally to the field of flow cells, more particularly, to a device for clamping a flow cell body to a flow cell retainer, and, even more particularly, to a device for clamping a flow cell body in to a flow cell retainer which, in turn, is mounted to a refractometer.

BACKGROUND OF THE INVENTION

Analysis of qualitative and quantitative aspects of interactions between analyte and various types of binding agents is paramount to a wide variety of scientific and industrial applications. As a result, many methods and for monitoring specific binding of sample analyte to a particular ligand have been developed.

Surface Plasmon Resonance (hereinafter "SPR") is one such method for monitoring the binding of an analyte with a ligand. SPR methods are generally based on the principle that, when a thin layer of metal is adhered to a glass surface having a specific index of refraction and illuminated with a beam of light having a specific angle of incidence, energy from the beam of light causes free electrons of the metal layer to become excited, resonate and form an electrical field, typically within 200 nanometers of the thin metal surface. Resonation of the excited free electrons of the thin metal surface, however, only occurs at certain angles of incidence and is dependent upon the refractive index of the thin metal layer. Consequently, because adhering substances to the thin metal layer can cause the index of refraction and the angle of incidence required to cause free electron resonance to change, the index of refraction and the angle of incidence required to cause resonation can be used to perform qualitative and quantitative analyses with regard to substances adhered to the thin metal layer. Indeed, one particularly well-suited use of SPR methods is for investigating binding and dissociation kinetics of analyte and ligand, as binding and dissociation of analyte alters the index of refraction of the thin metal surface and the angle of incidence required to cause free electron resonance.

One apparatus for investigating binding and dissociation of analyte and ligand via SPR generally comprise the use of a prism, a glass plate, and a flow cell body. Typically, a glass plate comprising a thin layer of gold is secured to a prism and separated by a thin layer of oil. Adhered to the thin gold layer is a ligand binding layer, which may comprise an antibody binding layer. A flow cell body comprising solution inputs and solution outputs and a gasket is then lowered to the surface of the glass. The gasket forms a sealed "flow cell" between the flow cell body and the glass plate such that a solution may be passed across the ligand binding layer via a solution input and solution output. As solution containing analyte (antigen) specific for the ligand (antibody) passes across the ligand binding layer, binding of analyte and ligand occurs, which causes a measurable change in the index of refraction of the thin film surface as well as a change in the angle of incidence required to cause resonance of the free electrons. Consequently, the changes can be used to perform qualitative and quantitative analysis of the analyte or ligand.

Heretofore, devices for securing a flow cell body to a glass plate and applying a force to create an effective seal have been limited. Indeed, most devices have required operators to secure the flow cell body via screws, wing nuts, or other similar means that typically require hand or tool tightening. Consequently, to change a flow cell body or a glass plate, the securing means are required to be removed by hand, a new flow cell body or surface inserted, and retightened. Completing all of these steps can be both time consuming and inefficient. In addition, hand tightening of the flow cell body does apply a consistent force to each flow cell body in successive assays such that proper arrangement of the flow cell body surface and sensor surface is provided. Thus, experimental error and/or inconsistencies between assays can occur.

In addition, another problem associated with current devices and methods for securing flow cell bodies is that the solution tubes create an obstacle to effective flow cell body clamping. Often, the solution tubes interfere, become entangled, or are inadvertently removed from the flow cell body, causing contamination and/or experimental error or failure. Thus, proper solution tube arrangement is required.

Hence, there has been a longfelt need for a simple and effective device for efficiently securing a flow cell body such that insertion or removal of the flow cell body is easily and efficiently provided, a relatively consistent force is applied to the flow cell body, and the clamping mechanism does not interfere with the solution tubes providing ingress and egress to the flow cell.

SUMMARY OF THE INVENTION

The present invention broadly comprises a flow cell clamp for clamping a flow cell body having a flow cell retainer. The flow cell clamp is operatively arranged to hold a flow cell body and a U-shaped clamping member is operatively arranged for applying a clamping force to the flow cell body and for holding the flow cell body securely within the flow cell retainer.

An object of the invention is to provide a device for efficiently and effectively clamping and removing a flow cell body from a measuring device.

Another object of the present invention to provide a device for applying a substantially consistent, constant and reproducible force to a flow cell body.

It is another object of the present invention to provide an effective means for arranging and disposing of flow cell solution tubes.

These and other objects, features and advantages of the present invention will become readily apparent to those having ordinary skill in the art upon a reading of the following detailed description of the invention in view of the drawings and claims.

BRIEF DESCRIPTION OF THE DRAWINGS

The nature and mode of operation of the present invention will now be more fully described in the following detailed description of the invention taken with the accompanying drawing figures, in which:

FIG. 8 is a sectional view of the clamping assembly, illustrating the U-shaped clamping member in the "clamped" and "unclamped" position, respectively.

DETAILED DESCRIPTION OF THE PREFERRED EMBODIMENT

While flow cells are particularly useful for performing analyses with regard to chemical and/or bio-based solutions, the applications of flow cells are many. Appropriately, it should be appreciated at the outset that, while in the detailed description that follows, we describe a flow cell clamp for use in combination with a device for performing Surface Plasmon Resonance, the specific combination presented herein is set forth merely to serve as an illustrative example. Indeed, the applications of the present invention are many and are not intended to be limited to use in a Surface Plasmon Resonance or other refractometer application. Nor is the device limited to optics applications. In fact, the present invention may be used alone, or with any type of instrument or measuring device wherein a flow cell body is required to be secured or clamped.

It should also be appreciated that, in the detailed description that follows, like reference numbers on different drawing views are intended to identify identical structural elements of the invention in the respective views. As used herein the term "consistent", as it applies to the present invention, is intended to refer to both a relatively constant force that may be applied to a flow cell body as well as to a relatively reproducible force that may be applied to each flow cell body in multiple assays. In the detailed description that follows, "U-shaped clamping member" is intended to generally refer to a device having a U-shaped appearance. For example, the U-shaped clamping member of the preferred embodiment comprises a pair of parallel and elongated members. However, it should be appreciated that a "U-shaped clamping member" may comprise non-elongated, non-parallel members; for example, a U-shaped member may appear stout and/or arcuate. Finally, in the detailed description that follows, the phrase "substantial contact", as it refers to a flow cell body, is intended to refer to a flow cell body in actual contact with, or proximate to, a glass surface, or surface to be analyzed.

Structure of a Flow Cell Clamp

Figure 1:
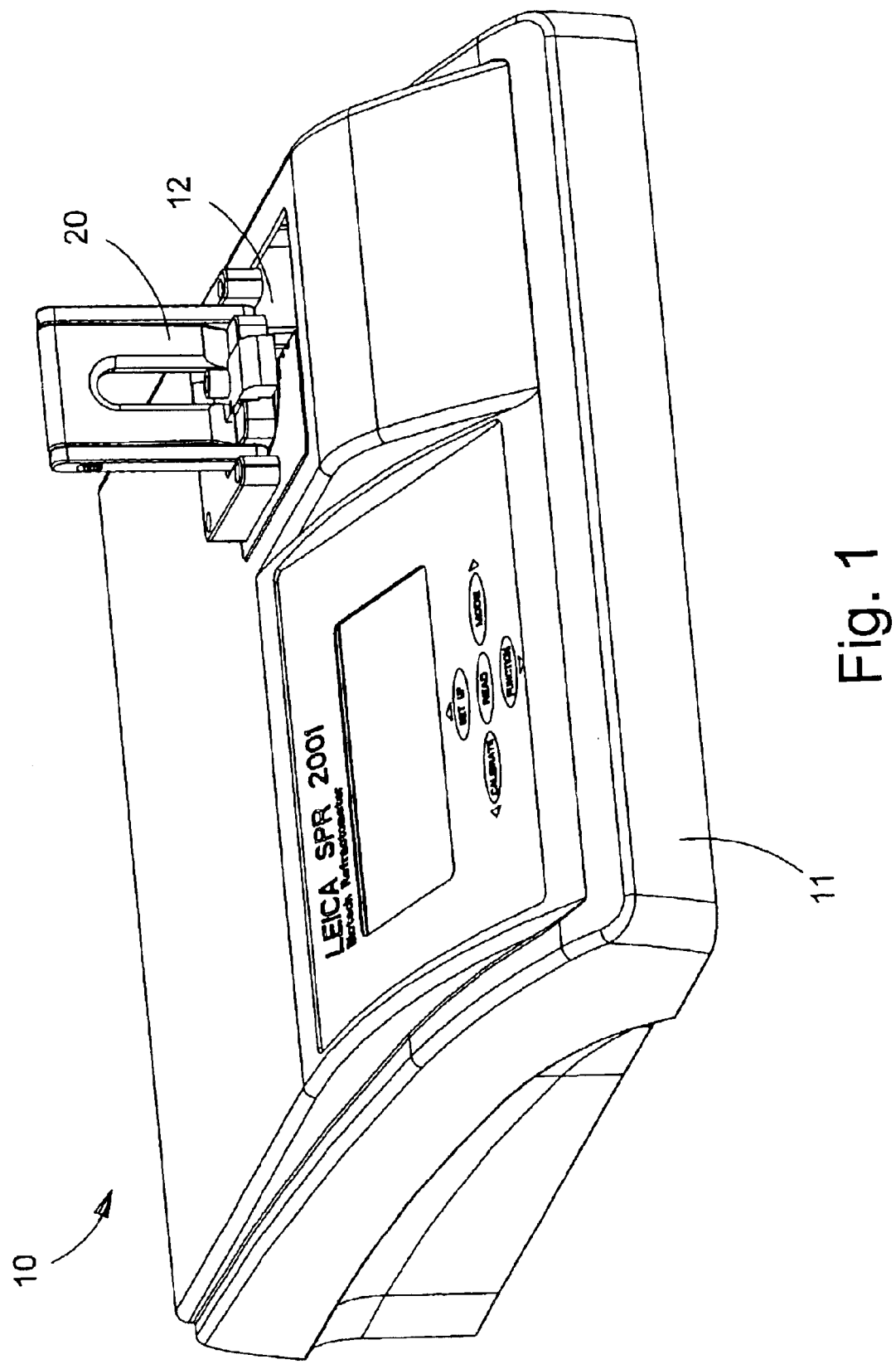
FIG. 1 is a perspective view of a preferred embodiment of the invention secured to an SPR measurement device.

FIG. 1 illustrates flow cell clamp assembly 20 of the present invention in combination with instrument 10 for performing Surface Plasmon Resonance. In this application, the flow cell clamp is used to secure a flow cell body to a device for measuring surface plasmon resonance. Instrument 10 generally comprises a refractometer 11 for measuring the index of refraction of a surface as well as the angle of incidence required for causing surface plasmon resonance of a particular surface. As is readily apparent, flow cell clamp assembly 20 of the present invention is generally secured to device 10 above optical analysis surface 12.

Figure 2:
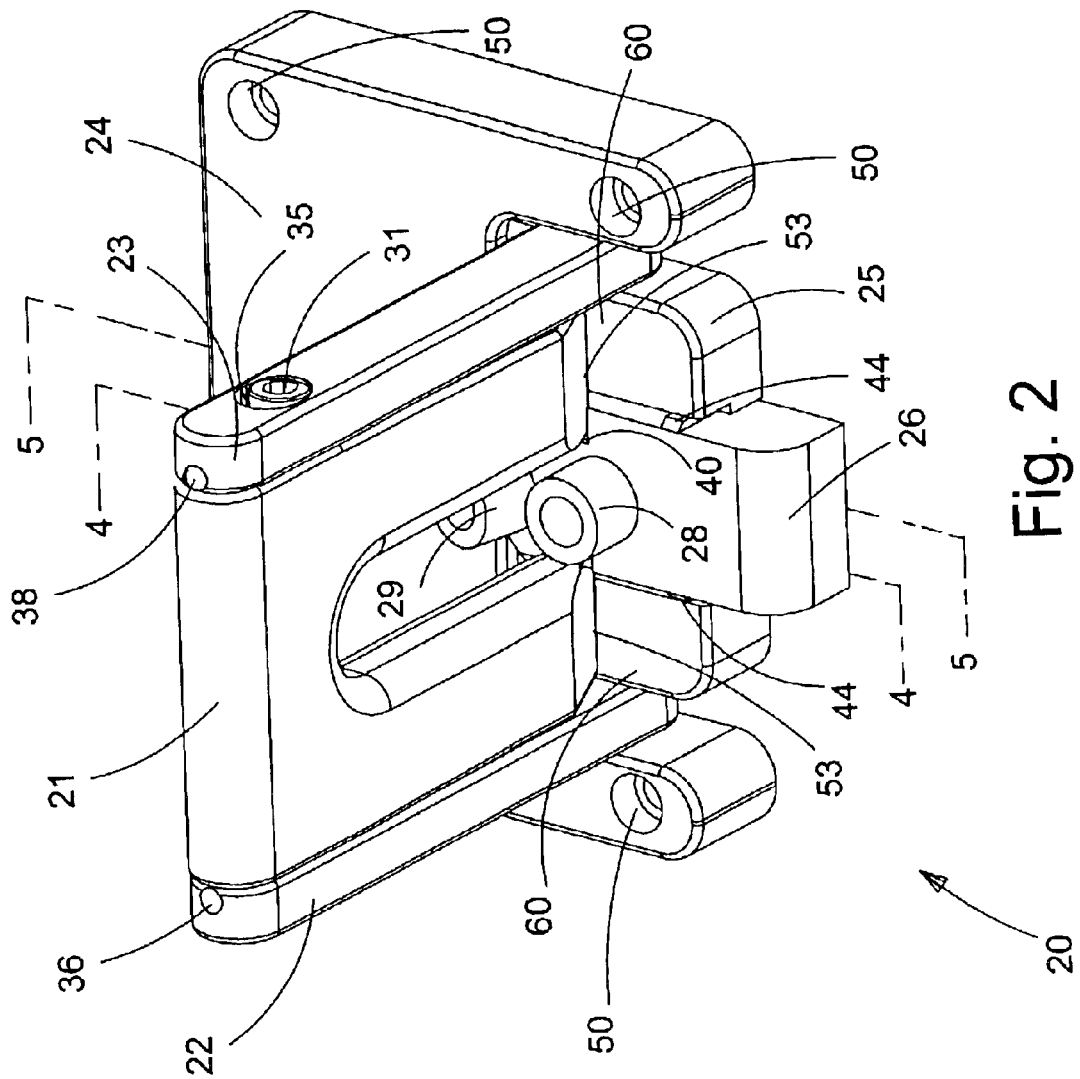
FIG. 2 is a perspective view of a preferred embodiment of the clamping assembly of the invention.
Figure 3:
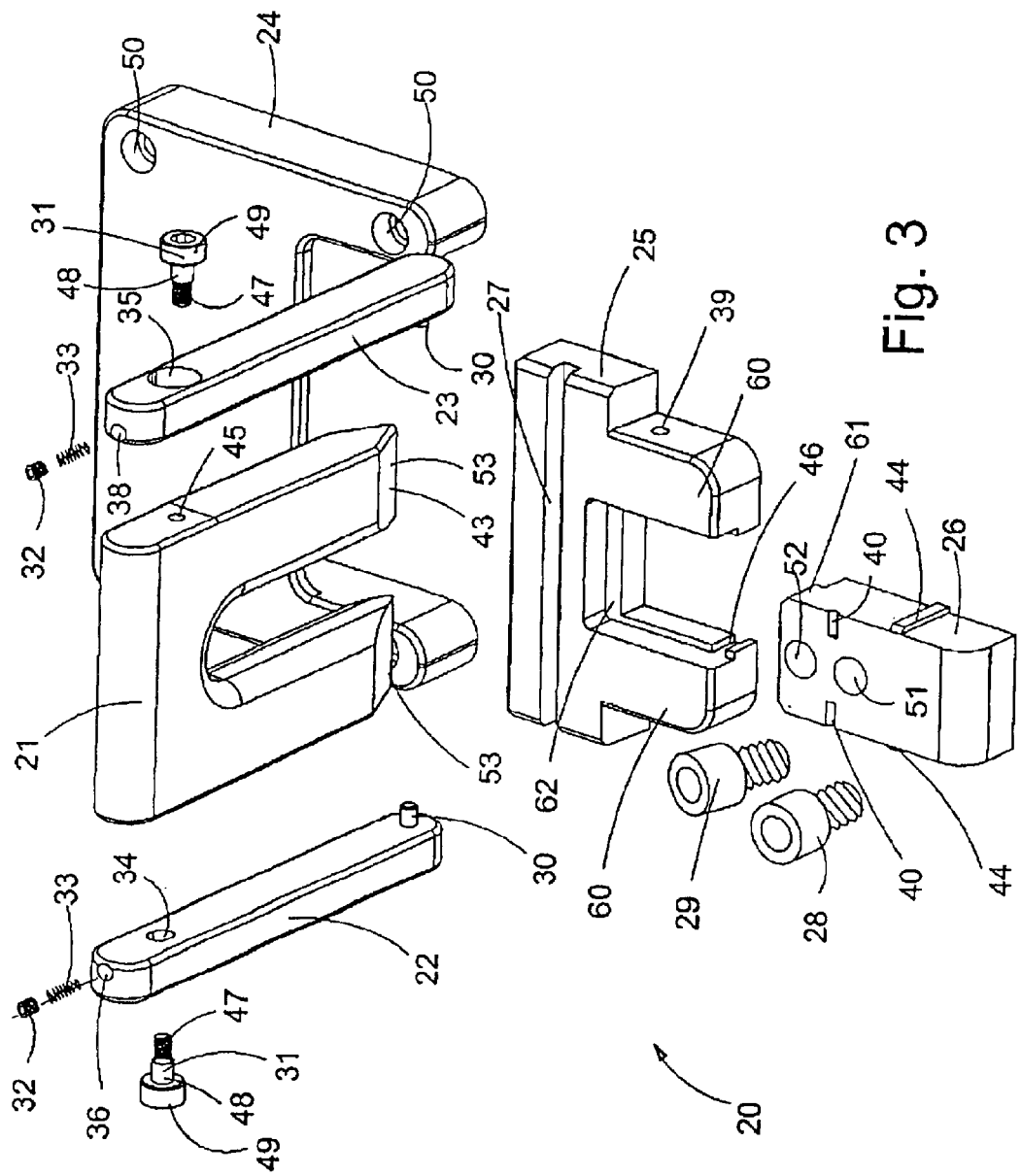
FIG. 3 is an exploded perspective view of the clamping assembling shown in FIG. 2.
Figure 4:
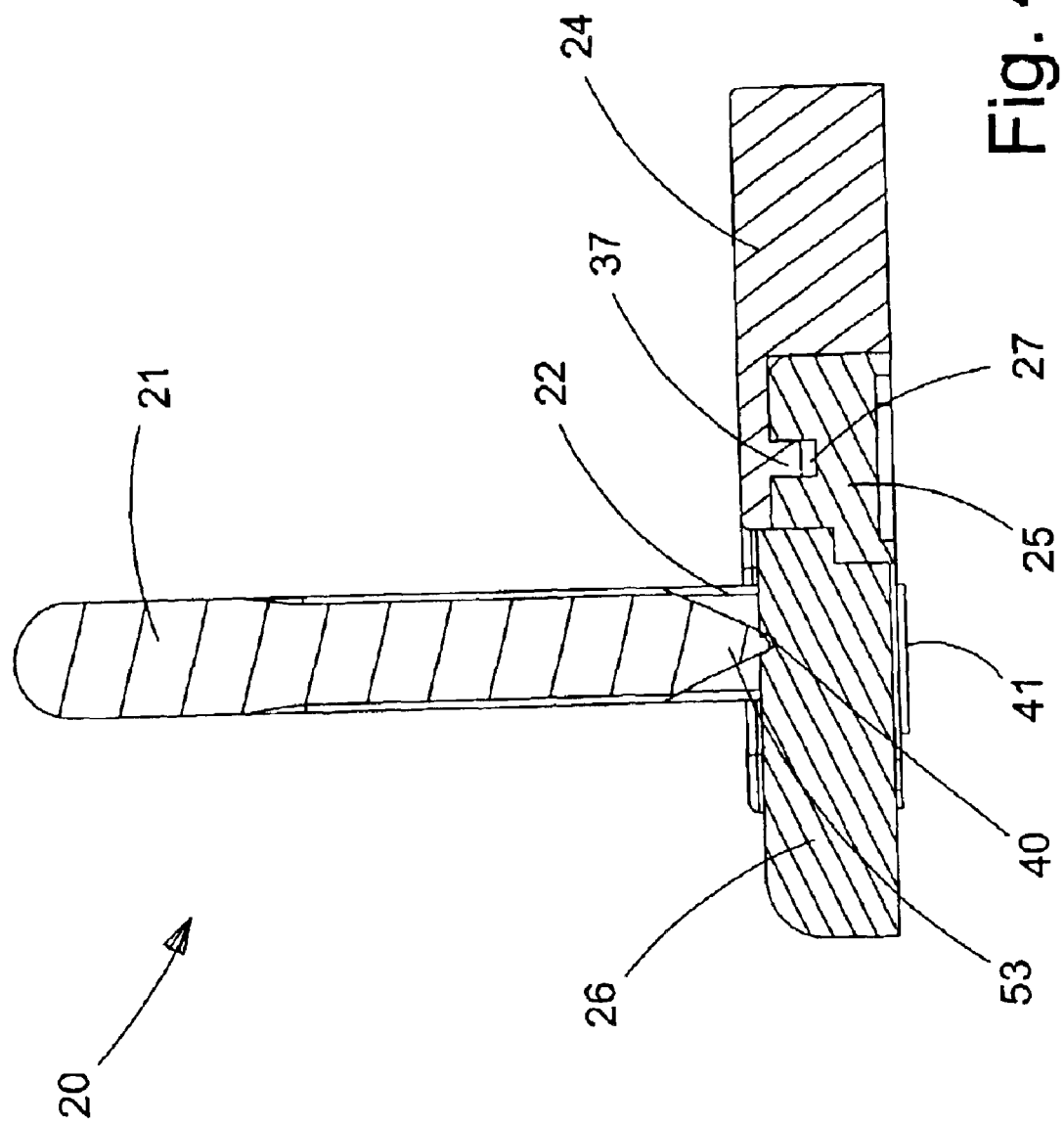
FIG. 4 is a sectional view of the clamping assembly taken generally along line 4—4 of FIG. 2.

As shown more clearly in FIGS. 2 and 3, flow cell clamp assembly 20 generally comprises flow cell retainer 25 operatively arranged to hold flow cell body 26, and U-shaped clamping member 21 operatively arranged to apply a clamping force to flow cell body 26 to hold the body securely within the flow cell retainer. As shown in the drawings, flow cell clamp assembly 20 may further comprise mounting means 24, which secures the flow cell clamp to the refractometer. Mounting means 24 generally comprises counterbores 50 for securing the mounting means and flow cell clamp assembly by means of threaded bolts or other like means. It should be appreciated by those having skill in the art that other means of securing the flow cell clamp assembly to a device are contemplated, which means do not depart from the spirit and scope of the invention. Mounting means 24 is also operatively arranged for engaging and releasably securing flow cell retainer 25. Hence, mounting means 24 comprises tongue 37 (shown in FIGS. 4 and 5), which is operatively arranged for communication and engagement with groove 27 of flow cell retainer 25.

Flow cell retainer 25 comprises a reshaped structure that is provided for securing flow cell body 26. Flow cell retainer 25 generally comprises groove 27, pin partial through-bores 39 and retaining members 60. As is apparent, groove 27 is operatively arranged for communication with tongue 37 of mounting means 24 such that the flow cell retainer is secured by mounting means 24. Retaining members 60 are provided for securing flow cell body 26 such that translational movement of the flow cell body in the horizontal plane is prevented. Retaining members 60 additionally comprise vertically disposed grooves 46 for mating engagement with vertically disposed tongues 44 of flow cell body 26 for securing the flow cell body. Flow cell retainer 25 also comprises pin partial through-bores 39 for accepting pins 30 of support arms 22 and 23. The surfaces of pin partial through-bores 39 and pins 30 are machined such that the support arms 22 and 23 rotate relative to the flow cell retainer.

Figure 9:
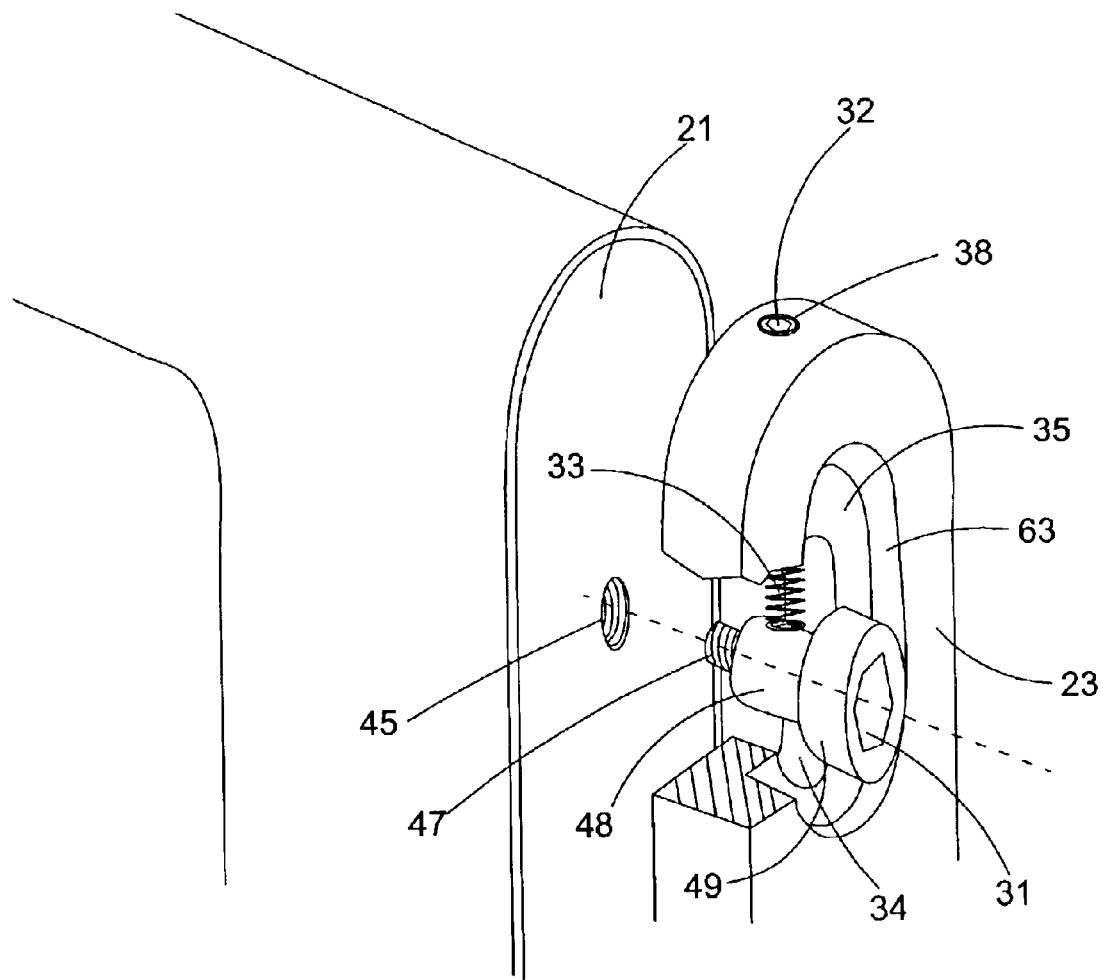
FIG. 9 is a partially exploded fragmentary view of a portion of a support arm of the clamping assembly, illustrating the shoulder bolt and channels for providing translational and rotational movement of the U-shaped clamping member.

Support arms 22 and 23 are generally provided for supporting the U-shaped clamping member. Pins 30 protrude outwardly from a lower end of each support arm, and, as described previously, are arranged for rotational engagement with pin partial through-bores 39. Support arms 22 and 23 additionally comprise elongated counterbores 63 comprising outer partial-through-bores 35, for accepting bolt heads 49, and inner through-bores 34, for accepting bolt shoulders 48. As shown in FIGS. 8 and 9, outer partial through-bores 35 and inner through-bores 34 of elongated counterbores 63 are operatively arranged to allow bolt heads 49 and bolt shoulders 48, respectively, to slide therein. At an upper lateral end of each inner through-bore 34, and operatively arranged for communication therewith, are threaded through-bores 36 and 38, whose through-bore axes are perpendicular to those of elongated counterbores 63. Threaded through-bores 36 and 38 are operatively arranged to accept compression springs 33, which are secured therein by means of bolts 32. Compression springs 33, thus, are disposed between bolts 32 and bolt shoulders 48. Consequently, springs 33 are operatively arranged to bias shoulder bolts 31.

U-shaped clamping member 21 generally comprises elongated members 43, each comprising a tooth 53. U-shaped clamping member 21 also comprises threaded bores 45, for rotationally engaging threads 47 of shoulder bolts 31. Thus, shoulder bolts 31 secure U-shaped clamping member 21 to support arms 22, 23 while simultaneously permitting rotation of U-shaped clamping member 21 relative thereto. It should be appreciated that in a fully tightened position, the rotation of U-shaped clamping member 21 with respect to support arms 22 and 23 causes rotation of shoulder bolts 31 within elongated counterbores 63. It should also be appreciated that in a fully tightened position, bias from springs 33 act upon shoulders 48 of shoulder bolts 31 such that bias is transferred to U-shaped clamping member 21. Bias transferred to U-shaped clamping member 21, thus, causes teeth 53 of U-shaped clamping member 21 to assert a force upon flow cell body 26, when U-shaped clamping member is in the "clamped" or "up" position. Thus, as is apparent, U-shaped clamping member 21 is generally structured to maintain a substantially vertical orientation when applying a force upon flow cell body 26. Nevertheless, it should be appreciated by those having skill in the art that U-shaped clamping member 21 may also be configured to apply a force when maintaining a substantially horizontal position. It should also be appreciated by those having skill in the art that U-shaped clamping member 21 generally allows solution flow tubes (not shown) to be easily inserted into threaded tube ports 28 and 29 while simultaneously asserting a force upon flow cell body 26. In addition, as is readily apparent "free-space" portion of U-shaped clamping member 21 provides relatively easy access to tube ports 28 and 29 and prevents the solution flow tubes from becoming entangled with one another. Finally, U-shaped clamping member 21 allows an operator to efficiently arrange the solution flow tubes such that the flow cell body may be readily changed.

Figure 6:
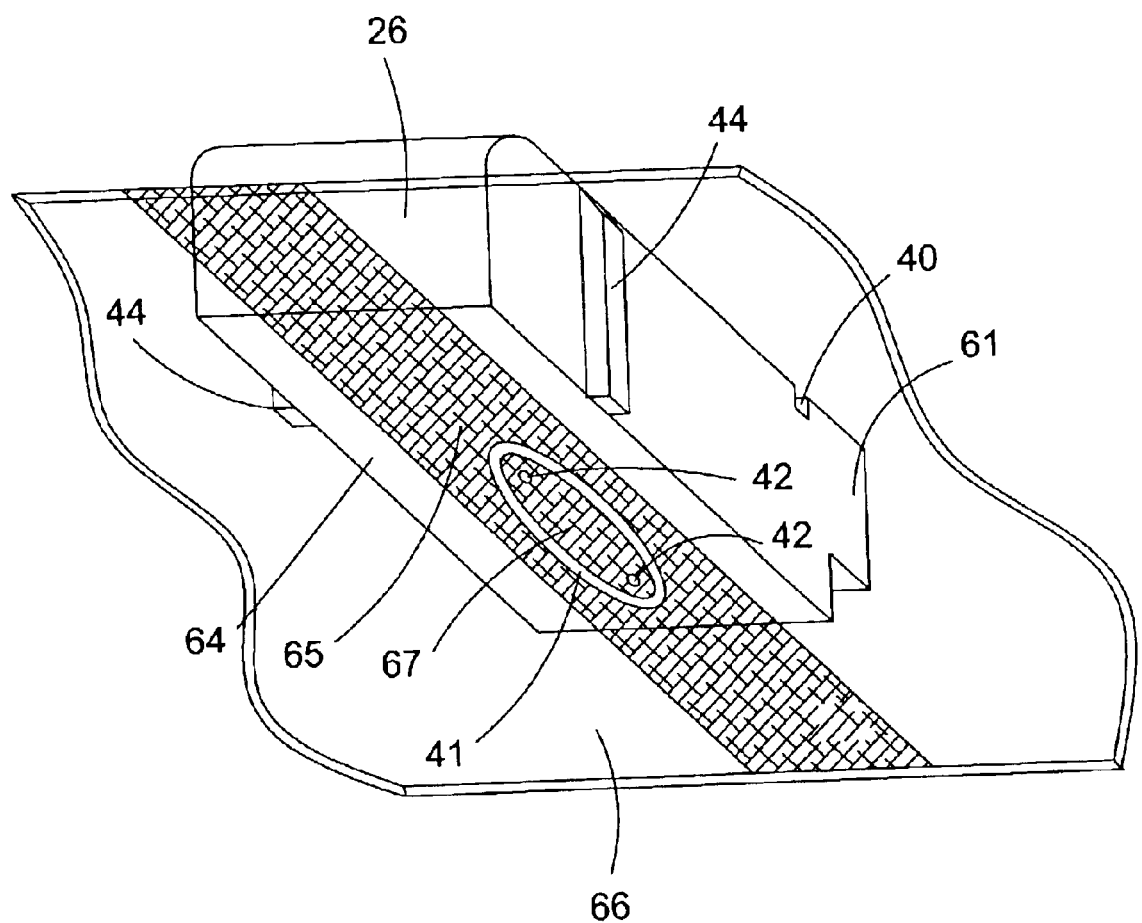
FIG. 6 is a perspective view of the flow cell body.

Referring now to FIGS. 2, 3 and 6, flow cell body 26 is operatively arranged for insertion into flow cell retainer 25 and configured for communication and engagement with U-shaped clamping member 21 such that the flow cell body may be effectively secured to glass plate 66, or like surface. Flow cell body 26 additionally comprises detents 40 for engaging teeth 53 of U-shaped clamping member 21 as well as vertically oriented tongues 44. Vertically oriented tongues 44 are operatively arranged for communication and engagement with vertically oriented grooves 46 of flow cell retainer 25, such that the flow cell body is properly disposed and secured in the flow cell retainer. Flow cell body 26 additionally comprises protruding abutment wall 61, which is operatively arranged for communication with recessed wall 62 of flow cell retainer 25 such that proper vertical orientation of the flow cell body is maintained with respect to the flow cell retainer.

Figure 5:
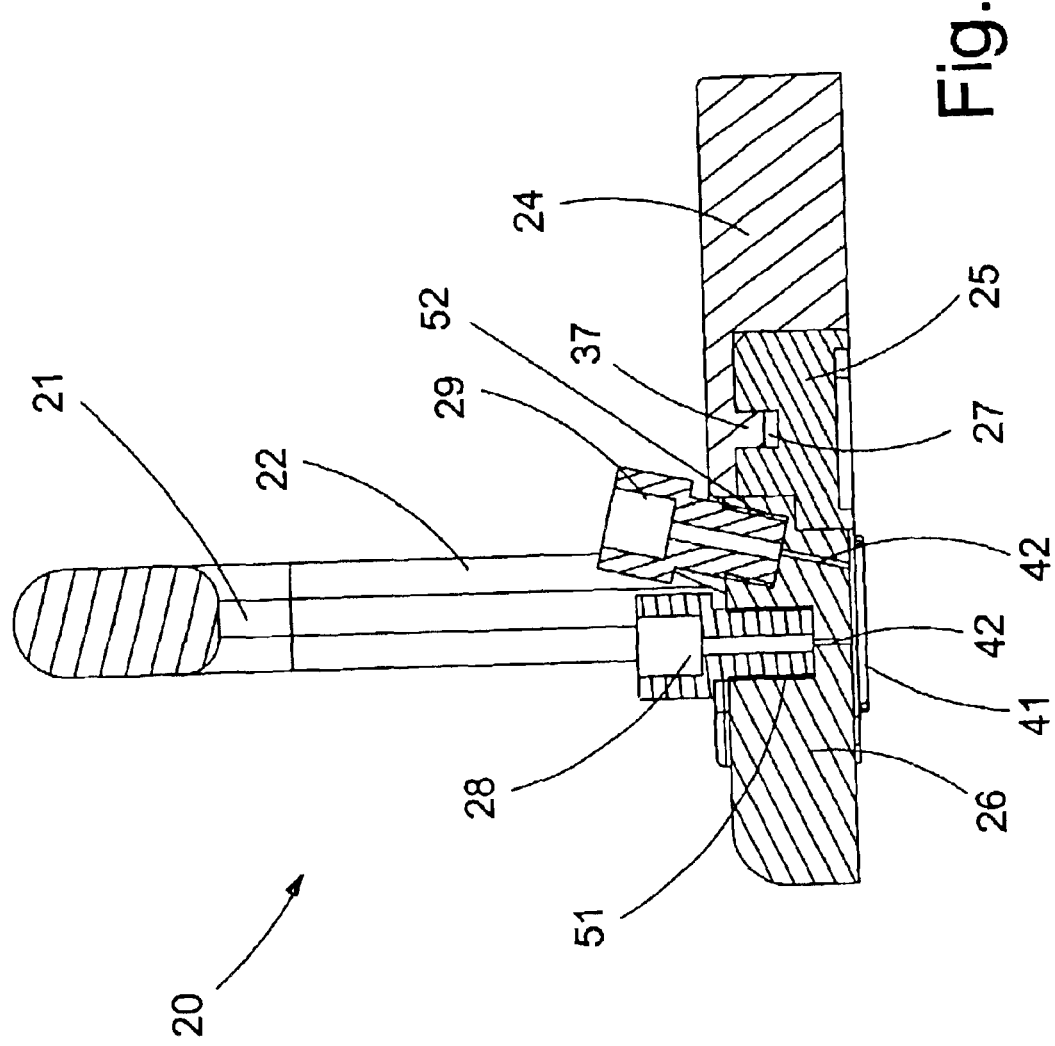
FIG. 5 is a sectional view of the clamping assembly taken generally along line 5—5 of FIG. 2.

Referring now to FIGS. 5 and 6, flow cell body 26 is operatively arranged for forming flow cell 67 and passing a solution to be analyzed between bottom surface 64 of the flow cell body and binding layer 65 of glass plate 66. Flow cell 67 is generally formed by placing and securing O-ring gasket 41 between bottom surface 64 of flow cell body 26 and binding layer 65 of glass plate 66 opposite threaded tube ports 28 and 29. Flow cell body 26 also comprises threaded bores 51 and 52 for threadable engagement with threaded tube ports 28 and 29. Threaded tube ports 28 and 29 may be either solution inputs and/or outputs. Threaded tube ports are operatively arranged for accepting solution flow tubes (not shown), which pass solution to be analyzed through the flow cell body. As is apparent, threaded tube ports 28 and 29 and threaded bores 51 and 52 communicate with solution passageways 42 (shown in FIG. 5) for passing a solution across binding layer 67 of flow cell 67. Hence, a solution to be analyzed may be passed across binding layer 65 and between solution passageways 42 via flow cell 67.

Operation of Apparatus

For purposes of illustration we describe the operation of the flow cell clamp of the present invention in association with a device for measuring surface plasmon resonance; it should be appreciated, however, that other applications of the present invention are contemplated. Indeed, the present invention may be used in any type of application wherein a flow cell may need to be secured.

Flow cell clamp assembly 20 is generally structured such that it may be secured to a refractometer and is also structured to apply a constant or consistent force upon a flow cell body. The structure of flow cell clamp assembly 20 also allows flow cell bodies to be efficiently inserted and removed and prevents solution flow tubes extending from the flow cell body from obstructing experimental procedures.

Figure 7:
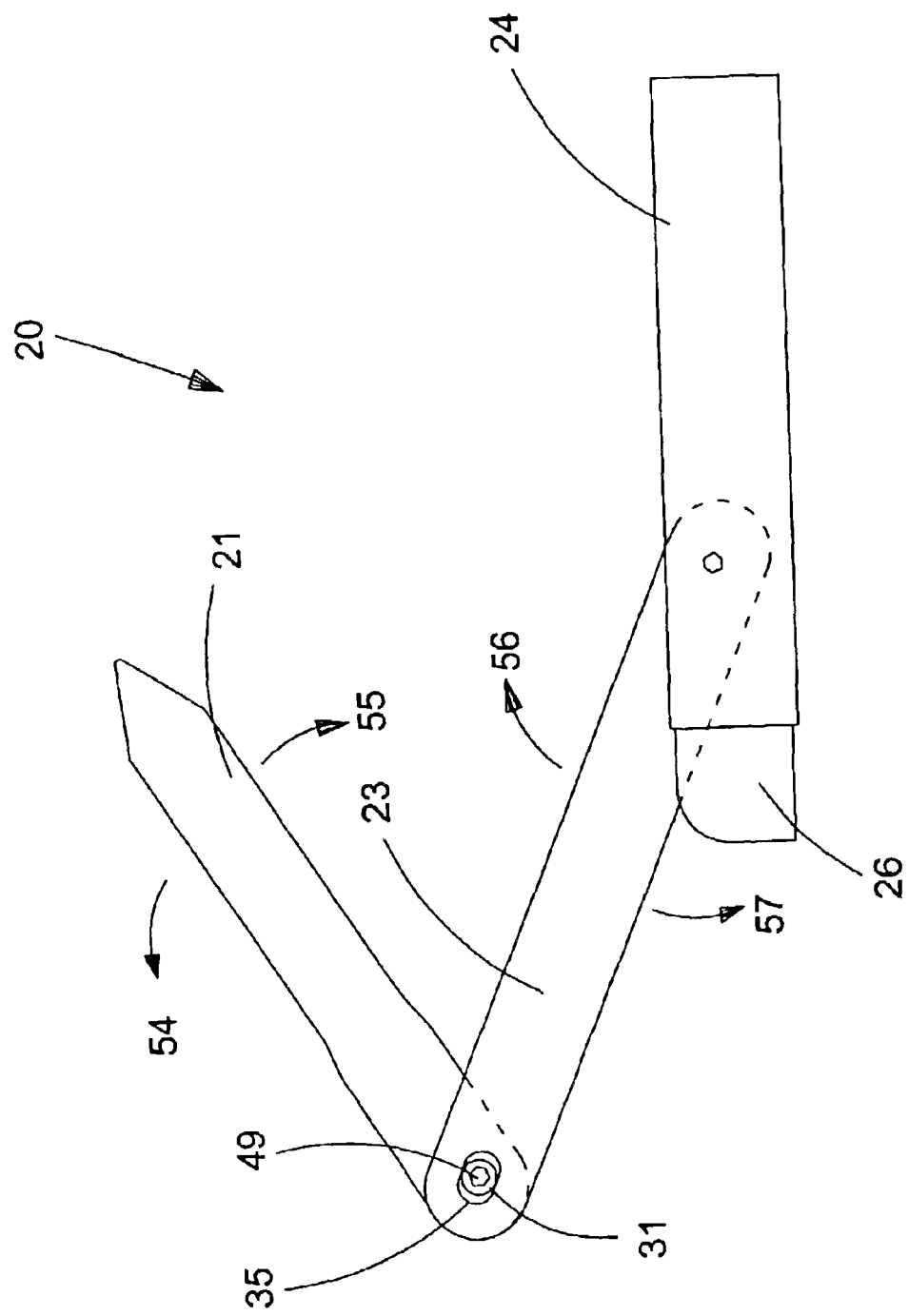
FIG. 7 is a side view of the clamping assembly, illustrating the U-shaped clamping member and associated support arms in an open, "unclamped" position.

Adverting now to FIG. 7, flow cell clamp assembly 20 of the present invention may be "folded" and "unfolded", to and from "clamped" and "unclamped" positions, respectively. Clamping and unclamping of the flow cell clamp assembly allows the easy insertion or removal of a flow cell body from flow cell retainer 25. Clamping also applies a consistent force to a flow cell body and allows solution flow tubes to be easily changed and arranged. Folding and unfolding of flow cell clamp 20 is generally provided by means of two pivot points.

One pivot point comprises pins 30 and pin partial through-bores 39, which are operatively arranged for rotational engagement with one another such that support arms 22 and 23 rotate relative to flow cell retainer 26. As shown in more detail in FIGS. 3 and 7, pins 30 and pin partial through-bores 39 have machined surfaces such that support arms 22 and 23 may be easily rotated in directions 56 and 57. As is apparent "unfolding" of the support arms occurs in direction 57 and "folding" occurs in direction 56 to cause "unclamping" and "clamping" of the flow cell body 26.

Another pivot point comprises shoulder bolts 31 and partial threaded bores 45, which are operatively arranged for securing U-shaped clamping member 21 to support arms 22 and 23 as well as for permitting rotation of the U-shaped clamping member relative thereto. As shown in FIG. 9, threaded portions 47 of shoulder bolts 31 are operatively arranged for threadable engagement with threaded bores 45 of U-shaped clamping member 21. Referring now to FIGS. 7–9, outer partial through-bores 35, inner through-bores 34, bolt heads 49 and bolt shoulders 48, respectively, are operatively arranged for communication such that pivoting of U-shaped clamping member 21 relative to support arms 22 and 23 is provided. Outer partial through-bores 35 and inner through-bores 34 are elongated and machined such that shoulder bolts 31 may slide therein. As shown in more detail in FIGS. 3a, 8 and 9, bolt heads 49 of shoulder bolts 31 are smooth and operatively arranged for translational and rotational movement within outer partial through-bores 35. Similarly, bolt shoulders 48 of shoulder bolts 31 are smooth and operatively arranged for translational and rotational movement within inner through-bores 34. Thus, rotation of U-shaped clamping member 21 relative to the support arms, in directions 54 and 55 is provided for "unfolding" and "folding" the flow cell clamp assembly. It should be appreciated, however, that free movement of shoulder bolts 31 within elongated counterbores 63 is partially inhibited by means compression springs 33, which assert a biasing force on bolt shoulders 48 of shoulder bolts 31.

Referring now to FIGS. 8 and 9; compression springs 33 are provided for biasing shoulder bolts 31, which bias asserts a force upon U-shaped clamping member 21. Force transferred to U-shaped clamping member 21 generally causes U-shaped clamping member 21 to assert a force in direction 58 (shown in FIG. 8). U-shaped clamping member, thus, is caused to assert a force upon an inserted flow cell body. As is evident from FIG. 8, in the "clamped" position, bias provided by springs 33 causes teeth 53 of U-shaped clamping member to engage detents 40 of flow cell body 26, such that the flow cell body is secured in place. Additionally, it should be appreciated that in the "clamped" position, flow cell body asserts an opposing force in direction 59, which counters the bias provided by springs 33. As shown in more detail in FIG. 8, opposing force 59 provided by flow cell body 26, causes shoulder bolts 31 to slightly compress springs 33. However, in an "unclamped" position, opposing force 59 is not generated and the compression springs are allowed to fully bias shoulder bolts 31.

As shown in FIG. 7, "unfolding" or "unclamping" of the flow cell clamp assembly occurs relative to the "up" position, wherein the "up" position refers to that position where U-shaped clamping member is substantially vertical as shown in FIGS. 1, 2, 4 and 5. Starting from the "up" position, rotation of the support arms in direction 57 releases teeth 53 of the U-shaped clamping member from detents 40. As the teeth are released from the detents, force 58 applied to the flow cell body is ceases. Continued rotation of the arms, in turn, causes teeth 53 of the U-shaped clamping member to rotate upwardly, in direction 54. Further rotation (as shown in FIG. 7) of the U-shaped member in direction 54, to its rotational limit results in a complete "unfolded" position.

As shown in FIG. 7, "folding" of the flow cell clamp occurs relative to a substantially "unfolded" position. Upon insertion or removal of a flow cell body (herein we refer to insertion) and starting from the unfolded position, U-shaped clamping member 21 is lifted and rotated in direction 55 until it contacts flow cell body 26. Upon contact with flow cell body 26, support arms 22 and 23 are lifted and rotated in direction 56 such that teeth 53 of U-shaped clamping member 21 are caused to contact and slide across the upper surface of the flow cell body. Sliding of teeth 53 across flow cell body 26 is caused until the teeth engage detents 40. Upon engaging detents 40, sliding of the teeth along the upper surface of the flow cell body is ceased and the continued upward rotation of support arms 22 and 23 in direction 56 causes biasing force of compression springs 33 (which is transmitted through shoulder bolts 31 and into teeth 53 of U-shaped clamping member 21) to act upon flow cell body 26 in direction 58. Force applied upon flow cell body 26, thus, secures the flow cell body within the flow cell retainer and also causes gasket 41 to compress such that a seal is formed between the lower, open surface of the flow cell body and the surface to be measured, thereby creating a flow cell.

Thus, as is apparent, flow cell clamp assembly 20 is particularly well suited for efficiently and effectively securing a flow cell body to a surface to be measured such that a flow cell may be created between the lower, open surface of flow cell body 26 and the binding layer of a measuring surface. Hence, a solution to be analyzed may be passed between the binding layer and the lower, open surface of the flow cell body such that a constant flow of solution across the binding layer may be obtained. It should be appreciated that flow cell clamp assembly 20 is efficiently and effectively configured for arranging flow cell solution tubes and allowing the easy exchange of the flow cell body between various assays.

Finally, while we describe a flow cell clamp assembly in combination with a device for performing surface plasmon resonance, it should be appreciated by those having skill in the art, however, that other applications of the present invention are contemplated, which applications do not depart from the scope of the invention as claimed.

What I claim is:

1. A flow cell assembly comprising:
    a flow cell body including at least one flow tube bore and a pair of detents;
    a flow cell retainer including an opening for receiving at least a portion of the flow cell body;
    a U-shaped clamping member having a pair of elongated legs spaced apart to simultaneously engage the pair of detents of the flow cell body, wherein the U-shaped clamping member defines open space allowing access to the at least one flow tube bore;
    at least one support arm pivotally coupled to the flow cell retainer at a first location along the support arm and pivotally coupled to the U-shaped clamping member at a second location along the support arm, wherein the second location is spaced from and slidably adjustable relative to the first location; and
    a spring arranged to urge the second location toward the first location.

2. The flow cell assembly according to claim 1, wherein the at least one support arm comprises a pair of the support arms on opposite sides of the flow cell retainer.

3. The flow cell assembly according to claim 2, wherein each of the pair of detents is in the form of a groove, and each of the pair of elongated legs of the of the U-shaped clamping member terminates in a tapered tooth adapted to engage the corresponding groove.

4. The flow cell assembly according to claim 1, wherein the at least one support arm is pivotally coupled to the U-shaped clamping member by a fastener extending through an elongated slot in the at least one support arm, and the spring acts between the fastener and the at least one support arm.

* * * * *

UNITED STATES PATENT AND TRADEMARK OFFICE
CERTIFICATE OF CORRECTION

PATENT NO. : 6,816,254 B2 Page 1 of 1
DATED : November 9, 2004
INVENTOR(S) : Lawrence R. Pastwik It is certified that error appears in the above-identified patent and that said Letters Patent is hereby corrected as shown below:

<u>Title page,</u>
Item [73], Assignee, should read:
-- Reichert, Inc. --.

Signed and Sealed this

Eighth Day of February, 2005

JON W. DUDAS
*Director of the United States Patent and Trademark Office*